United States Patent [19]
Yeh et al.

[11] 4,267,164
[45] May 12, 1981

[54] EFFERVESCENT STANNOUS FLUORIDE TABLET

[75] Inventors: Kuo-Chen Yeh, Westfield, N.J.; Frank Mazzella, Brooklyn, N.Y.

[73] Assignee: Block Drug Company Inc., Jersey City, N.J.

[21] Appl. No.: 117,124

[22] Filed: Jan. 31, 1980

[51] Int. Cl.$^3$ .............. A61K 7/18; A61K 9/46; A61K 33/16
[52] U.S. Cl. ................ 424/44; 424/52; 424/151
[58] Field of Search .................. 424/49–58, 424/44, 151

[56] References Cited

U.S. PATENT DOCUMENTS

| | | | |
|---|---|---|---|
| 3,282,792 | 11/1966 | Fiscella | 424/52 |
| 3,518,343 | 6/1970 | Welsh et al. | 424/44 |
| 3,937,806 | 2/1976 | Cooley | 424/52 |
| 4,042,680 | 8/1977 | Muhler et al. | 424/55 |
| 4,108,981 | 8/1978 | Muhler et al. | 424/55 |
| 4,183,916 | 1/1980 | Rodon | 424/55 |

FOREIGN PATENT DOCUMENTS 2019658  5/1973  Fed. Rep. of Germany .......... 424/44

Primary Examiner—Shep K. Rose
Attorney, Agent, or Firm—Ostrolenk, Faber, Gerb & Soffen

[57] ABSTRACT

An effervescent tablet is produced by preparing a powdered tabletable composition containing stannous fluoride and malic acid and an alkali metal bicarbonate in a weight ratio of about 3:2 as the effervescent couple.

8 Claims, No Drawings

EFFERVESCENT STANNOUS FLUORIDE TABLET

BACKGROUND OF THE INVENTION

The presence of small amounts of fluoride in drinking water is commonly recognized to have a pronounced effect on reducing the incidence of dental caries in the permanent teeth of children. Fluoride salts have been introduced into public water supplies in many communities but this method of prophylaxis is not available to large numbers of people whose drinking water is obtained from fluoride deficient sources or where the addition of fluoride to common public water sources is not acceptable or permitted.

In 1950 Muhler et al. reported that stannous fluoride was more effective than 31 other compounds in preventing decalcification of powdered enamel in the laboratory. Radike and Muhler (1953) found that stannous fluoride reduced caries in hamsters by 51.2% in a topical and drinking water study while similar treatment with sodium fluoride resulted in only 26.3% reduction. Twenty years later, Radike et al. demonstrated the efficacy of a mouth rinse containing 250 ppm fluoride derived from stannous fluoride and in 1974, Corcoran reported that a stannous fluoride tablet yielding 200 ppm fluoride was effective as a caries prophylactic agent.

Limitations on the availability of fluoride therapy by means of the common water supply or by professional treatment has lead to extensive efforts to incorporate fluoride salts in dentrifices for use in the home. Toothpaste, however, often falls short of its cavity fighting mission because tooth brushing does not always reach the back teeth and the interproximal surfaces between teeth. It has been shown that 70% of all cavities occur in these areas.

Stannous fluoride is known to be subject to both oxidation and hydrolysis in aqueous solution to form the sparingly soluble stannous hydroxide which gives the solution a cloudy appearance and which is ineffective as an anti-caries agent. It is therefore not possible to formulate a stable aqueous stannous fluoride product and mouth rinse containing stannous fluoride must be used in a freshly prepared form.

Effervescent tablets which contain stannous fluoride were known prior to the present invention. For example, Welsh et al. in U.S. Pat. No. 3,518,343 shows water soluble tablets made by preparing an effervescent couple, a tableting lubricant and an antimicrobial substance which can optionally contain stannous fluoride. The effervescent couple includes a solid acid such as malic, fumaric, tartaric, itaconic, maleic, citric or mesaconic acid, and a solid base such as an alkali or alkaline earth carbonate or bicarbonate which, when dissolved in water, react to produce effervescence. One example of this patent discloses a stannous fluoride tablet employing citric acid and sodium bicarbonate in a weight ratio of about 2:3 as the effervescent couple.

It is the object of this invention to provide an effervescent tablet which will maintain the chemical integrity of the stannous fluoride anti-caries agent and rapidly dissolve in water to provide a stannous fluoride mouthrinse having a superior anti-caries potential. This and other objects of the invention will become apparent to those skilled in the art from the following detailed description.

SUMMARY OF THE INVENTION

This invention relates to the preparation and the composition of a water soluble, effervescent table containing stannous fluoride as an anti-caries agent. More particularly, the tablet contains malic acid and an alkali metal bicarbonate in a weight ratio of about 3:2 as the effervescent couple thereby providing a higher fluoride ion uptake by human enamel. The invention also concerns the use of a highly effective lubricant system.

DESCRIPTION OF THE INVENTION

The effervescent tablet of the present invention contains about 1–10% by weight, preferably about 2–9% by weight of stannous fluoride and about 50–70%, preferably about 60–72% by weight of an effervescent couple which is malic acid and an alkali metal bicarbonate in a weight ratio of about 3:2. The alkali metal bicarbonate is preferably sodium bicarbonate.

The use of malic acid as the solid acid in the effervescent couple provides superior results to the use of, e.g. citric acid. The prime mode of dental caries attack is the acid dissolution of tooth structure and therefore one of the most frequently adopted criteria for the evaluation of the anti-caries activity of an agent has been the Enamel Solubility Reduction test. A tablet of the present invention employing malic acid as one of the effervescent couple produced an average ESR of $52 \pm 2\%$ while another tablet having the same ingredients and prepared in the same way except for replacement of the malic acid with citric acid, at an average ESR of 40%. The testing of a leading commercially available stannous flouride toothpaste produced an average ESR of only 38%.

It has also been found that a tablet of the present invention (malic acid/alkali metal bicarbonate ratio 3:2) provides a higher fluoride ion uptake by human enamel than a tablet in which the malic acid/bicarbonate ratio is about 2:3.

The difference in fluoride ion uptake is statistically significant ($P < 0.09$).

The effervescent tablet of the present invention can contain the conventional tableting aids, lubricants, coloring agents, sweeteners, flavoring agents, and the like in accordance with the general practice in the art of effervescent tablet.

The amount of the tableting aid can generally be about 10–50% by weight. It is preferred, however, that the tablet of the present invention have a dissolution time of about 30–90 seconds, preferably about 50–70 seconds, in order to serve as a timer for the individual user, particularly children, to adequately clean their teeth. In order to achieve such a tablet dissolution time and to obtain a tablet of acceptable hardness with no evidence of capping or laminating, it is necessary to employ a minimum level of a satisfactory tableting aid and also to ensure that the combination of ingredients have compatible particle size distribution. In accordance with these considerations, it has been found that sorbitol is superior to other hexose sugars and it is therefore the tableting aid of choice. Sorbitol is, as are the other ingredients in the instant tablet, water soluble and non-cariogenic.

Furthermore, in order to achieve a tablet dissolution time of most preferably about 50–70 seconds, the hardness of the tablet upon manufacture should be no greater than 5 SCHU. A highly effective lubricant system is necessary in order to achieve this relatively low tablet hardness and still prevent sticking to the die walls and punch faces of the tablet press. A two part solid lubricating system has been found to be particularly appropriate. One part of the system is a high molecular weight solid polyethylene glycol, i.e. a polyethylene glycol whose molecular weight is between 6000–7500. A commercially available polyethylene glycol having a 6000 molecular weight is preferred and is used at a concentration of about 2–10%, preferably about 3–5% of the total tablet weight. The second part of the solid lubricating system constitutes about 0.1–0.5, preferably about 0.1–0.2% of the total tablet weight and is a siloxane polymer, preferably simethicone. The finely divided sodium benzoate, preferably −100 mesh, is coated with about 1–4% simethicone, preferably about 2–3% simethicone, is prepared in any suitable equipment such as in a Patterson-Kelly solids processor by spraying an alcoholic slurry of the simethicone through the feed tube and intensifier bar and thereafter removing the alcohol by distillation.

The effervescent tablets of the present invention are prepared in the conventional procedure. For example, the solid, particulate, malic acid, sodium bicarbonate, sodium carbonate, stannous fluoride, polyethylene glycol 6000, simethicone on sodium benzoate, sorbitol, color additive, sweetener additive and flavor additive are introduced into a suitable mixer, such as a ribbon-type mixer, blended together and then compressed on a rotary press to form tablets which are shallow concave in shape, about 11.1 millimeters in diameter and weigh about 480–500 mg. Of course, other sizes, shapes and weights of tablets can be prepared if desired. In the preferred form, the tablets dissolve in about 50–70 seconds in 10 cc of 40° C. water to provide a stannous fluoride solution and containing about 0.1–0.4%, preferably about 0.1% stannous fluoride. The resulting solution is effective in preventing dental caries as shown before with reference to the In Vitro Enamel Solubility Reduction test and also demonstrated in an In vivo double blind animal caries study in which the tablet and a control were dissolved in fixed volumes of water and topically applied to the dentition of rats. The results achieved with the invention showed that the solution was significantly effective in reducing caries scores in that the amount of reduction on the sulcal surfaces was about 20%, on the buccal surfaces was about 34% and on the proximal was about 71%.

The following are typical of effervescent stannous fluoride tablets which can be prepared in accordance with the present invention.

TYPICAL FORMULATIONS

EXAMPLE I

| Ingredient | Weight Percent |
| --- | --- |
| Malic Acid | 42.0 |
| Alkali metal bicarbonate | 29.0 |
| Alkali metal carbonate | 7.00 |
| Stannous Fluoride | 2.10 |
| Colorant | 0.30 |
| Flavor | 2.00 |
| Sweetener | 0.40 |
| Sorbitol | 11.00 |
| Polyethylene Glycol | 3.00 |
| Sodium Benzoate | 3.00 |
| Siloxane Polymer | 0.20 |
| | 100.00 |

EXAMPLE II

| Ingredient | Weight Percent |
| --- | --- |
| Malic Acid | 41.0 |
| Alkali metal bicarbonate | 25.0 |
| Stannous Fluoride | 8.00 |
| Colorant | 0.40 |
| Flavor | 3.00 |
| Sweetener | 0.50 |
| Sorbitol | 12.00 |
| Polyethylene Glycol | 5.00 |
| Sodium Benzoate | 5.00 |
| Siloxane Polymer | 0.10 |
| | 100.00 |

EXAMPLE III

| Ingredient | Weight Percent |
| --- | --- |
| Malic Acid | 43.0 |
| Alkali metal bicarbonate | 28.0 |
| Stannous Fluoride | 4.00 |
| Colorant | 0.30 |
| Flavor | 2.00 |
| Sweetener | 0.60 |
| Sorbitol | 13.00 |
| Polyethylene Glycol | 4.00 |
| Sodium Benzoate | 5.00 |
| Siloxane Polymer | 0.10 |
| | 100.00 |

EXAMPLE IV

| Ingredient | Weight Percent |
| --- | --- |
| Malic Acid | 41.0 |
| Alkali metal bicarbonate | 26.0 |
| Stannous Fluoride | 2.50 |
| Colorant | 0.10 |
| Flavor | 2.00 |
| Sweetener | 0.20 |
| Sorbitol | 19.00 |
| Polyethylene Glycol | 3.00 |
| Sodium Benzoate | 6.00 |
| Siloxane Polymer | 0.20 |
| | 100.00 |

Various changes and modifications can be made in the effervescent stannous fluoride tablet of the present invention without departing from the spirit and scope thereof. The various embodiments which have been disclosed herein were for the purpose of further illustrating the invention but were not intended to limit it.

What is claimed is:

1. An effervescent stannous fluoride containing dental tablet comprising stannous fluoride and an effervescent couple consisting essentially of malic acid and an alkali metal bicarbonate in a weight ratio of about 3:2.

2. The effervescent tablet of claim 1 wherein said stannous fluoride comprises about 1–10% of said tablet, said effervescent couple is about 60–72% of said tablet and said alkali metal bicarbonate comprises sodium bicarbonate.

3. The effervescent tablet of claim 2 containing about 10–15 weight percent sorbitol as a tableting aid.

4. The effervescent tablet of claim 3 containing a lubricant comprising a solid polyethylene glycol of at least 6000 molecular weight and a siloxane polymer coated benzoate.

5. The effervescent tablet of claim 4 wherein said polyethylene glycol has a molecular weight of 6000 and is about 2–10% of the weight of the tablet and said siloxane polymer coated benzoate is about 2–8 weight percent simethicone coated sodium benzoate in which the simethicone is about 1–4 weight percent.

6. The effervescent tablet of claim 5 having a dissolution time of about 30–90 seconds in water, and a hardness of less than 5–6 SCHU.

7. The effervescent tablet of claim 6 in the form of an about 480–500 milligram slightly concave tablet of about 11.1 millimeters in diameter.

8. The effervescent tablet of claim 7 wherein the amount of said malic acid-bicarbonate effervescent couple is about 60–72%, the amount of the stannous fluoride is about 2–9%, the amount of the polyethylene glycol is about 3–5%, the amount of the simethicone on the sodium benzoate is about 2–4% and the amount of the simethicone coated sodium benzoate is about 3–6% percent, the sorbitol is about 10–20%.

* * * * *